(12) United States Patent
Muncie

(10) Patent No.: US 7,556,226 B2
(45) Date of Patent: Jul. 7, 2009

(54) INTRAVENOUS FLUID CONTAINER STAND

(76) Inventor: Cindy Muncie, 5922 Centerwood Dr., Crestwood, KY (US) 40014

( * ) Notice: Subject to any disclaimer, the term of this patent is extended or adjusted under 35 U.S.C. 154(b) by 0 days.

(21) Appl. No.: 11/469,993

(22) Filed: Sep. 5, 2006

(65) Prior Publication Data

US 2008/0054132 A1    Mar. 6, 2008

(51) Int. Cl.
  *F16M 11/00*    (2006.01)
(52) U.S. Cl. .................................. 248/176.1
(58) Field of Classification Search ............... 248/121, 248/127, 129, 176.1; 211/113, 117, 118, 211/85.5, 85.13, 205, 196
  See application file for complete search history.

(56) References Cited

U.S. PATENT DOCUMENTS

| | | | | |
|---|---|---|---|---|
| 1,261,755 A | * | 4/1918 | Forsyth | 248/125.8 |
| 1,606,354 A | * | 11/1926 | Fillion | 362/358 |
| 2,247,774 A | * | 7/1941 | Forsyth | 211/196 |
| 3,460,789 A | * | 8/1969 | Engelsher et al. | 248/146 |
| 3,547,275 A | * | 12/1970 | Engel | 211/205 |
| D290,196 S | * | 6/1987 | Miller | D6/415 |
| 4,725,027 A | | 2/1988 | Bekanich | |
| 4,832,294 A | * | 5/1989 | Eidem | 248/125.8 |
| 5,022,538 A | * | 6/1991 | Richmond et al. | 211/113 |
| D326,374 S | * | 5/1992 | Townsend | D6/412 |
| 5,135,191 A | | 8/1992 | Schmuhl | |
| D329,549 S | * | 9/1992 | Begley et al. | D6/412 |
| 5,421,548 A | * | 6/1995 | Bennett et al. | 248/129 |
| 5,480,036 A | * | 1/1996 | Opar | 211/45 |
| 5,487,476 A | * | 1/1996 | Barfield | 211/85.23 |
| D369,032 S | * | 4/1996 | Huang et al. | D6/412 |
| D372,156 S | * | 7/1996 | Botsford | D6/548 |
| 5,556,065 A | * | 9/1996 | Wadley | 248/129 |
| 6,375,133 B1 | | 4/2002 | Morrow | |
| 6,386,142 B1 | * | 5/2002 | Holscher et al. | 119/57.8 |
| 6,390,311 B1 | * | 5/2002 | Belokin | 211/204 |
| 2002/0096608 A1 | * | 7/2002 | Cedarberg, III | 248/125.3 |
| 2005/0120525 A1 | * | 6/2005 | Heil et al. | 27/1 |
| 2006/0070968 A1 | * | 4/2006 | Terhune et al. | 211/205 |

* cited by examiner

*Primary Examiner*—Kimberly T Wood
(74) *Attorney, Agent, or Firm*—Dale J. Ream

(57) ABSTRACT

An intravenous container stand according to the present invention includes an elongate pole having opposed upper and lower ends. The container stand includes a support member that may be selectively and removably coupled to the upper end of the pole. The support member includes a body portion coupled to the pole and at least one hook extending outwardly from the body portion for suspending an intravenous fluid container for delivery to the patient. A roller assembly, such a plurality of casters, may be coupled to the lower end of the pole for transporting the container stand to a desired location. The support member is selectively removable and replaceable, such as when different quantities of intravenous containers are needed or for the comfort and entertainment of a patient.

5 Claims, 4 Drawing Sheets

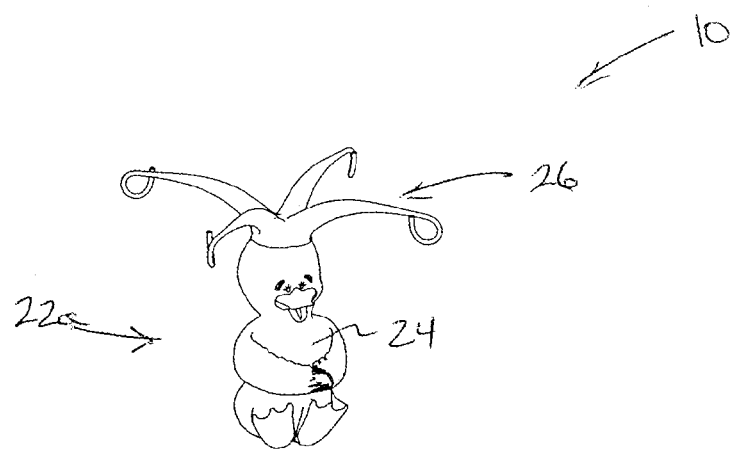
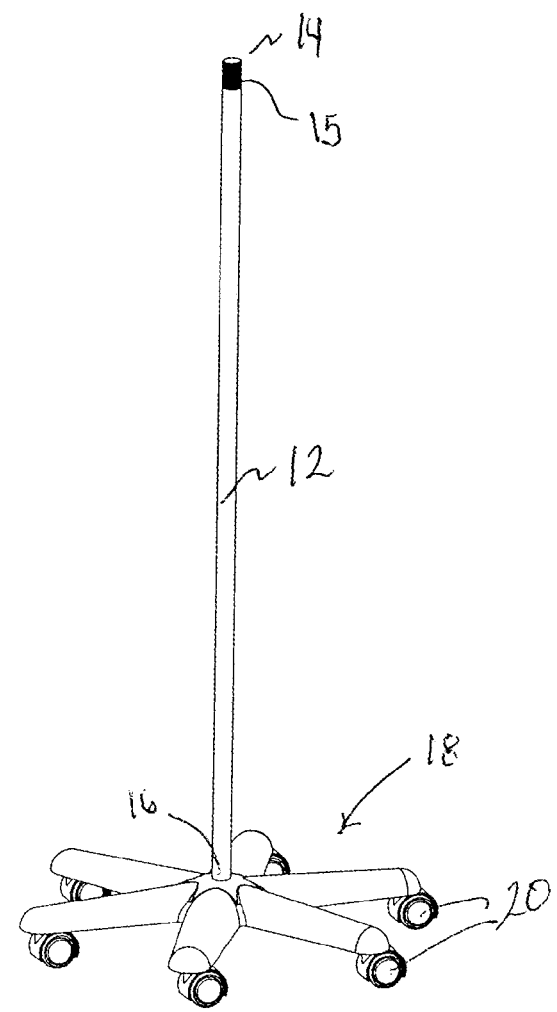
FIG. 2

INTRAVENOUS FLUID CONTAINER STAND

BACKGROUND OF THE INVENTION

This invention relates generally to medical equipment and, more particularly, to an intravenous fluid container stand having removable and interchangeable IV fluid container support members.

Stands having one or more hooks are traditionally used for holding intravenous bags of medicine or other fluids at the bedsides of patients in hospitals or other health facilities. Unfortunately, these stands can look quite intimidating, especially to children and particularly when many bags of medicine are in use simultaneously. In this case, it would be desirable to be able to remove the traditional bag-holding top portion and replace it with a bag holder having a configuration that is more comforting or even entertaining. Another reason for needing to remove and replace a traditional bag-holding support arm is if there are more bags that need to be suspended than the number of available hooks. Frequently, many fluid containers need to be in use at the same time and there may not be enough hooks from which to suspend the containers.

Various devices are known in the art for holding IV fluid containers. Although presumably effective for their intended purposes, the existing devices do not provide container-holding support arms that may be removed and replaced. Particularly, it would be desirable to have interchangeable bag-support arms having portions that provide comfort or entertainment to various age groups or categories of patients as well as portions that are functionally appropriate depending on the medical and emotional needs of various patients.

SUMMARY OF THE INVENTION

An intravenous fluid container stand according to the present invention includes an elongate pole having opposed upper and lower ends. The container stand includes a support member that may be selectively and removably coupled to the upper end of the pole. The support member includes a body portion coupled to the pole and at least one hook extending outwardly from the body portion for suspending an intravenous fluid container as the fluid, such as medicine, is being delivered to a patient. A roller assembly, such a plurality of casters, may be coupled to the lower end of the pole for transporting the container stand to a desired position.

The support member is removable and interchangeable in that support members having different utilities may be desired. For example, a traditional support member having a single hook capable of suspending a single intravenous fluid container may be desired on one occasion whereas a support member having multiple hooks may be desired in another circumstance, for example where multiple fluid containers are needed simultaneously. On still another occasion, a support member having a body portion indicative of an animal, a cartoon character, or some other likeness may be desired for the comfort, enjoyment, or general mental reassurance of a patient.

Therefore, a general object of this invention is to provide an intravenous fluid container stand having removable and interchangeable support arms for suspending respective containers of intravenous fluid.

Another object of this invention is to provide an intravenous fluid container having a support arm with a plurality of fluid container hooks.

Still another object of this invention is to provide an intravenous fluid container stand, as aforesaid, having a support arm configured as an animal or cartoon character.

Yet another object of this invention is to provide an intravenous fluid container stand, as aforesaid, having hooks that minimize inadvertent or accidental removal of IV fluid containers.

Other objects and advantages of the present invention will become apparent from the following description taken in connection with the accompanying drawings, wherein is set forth by way of illustration and example, embodiments of this invention.

BRIEF DESCRIPTION OF THE DRAWINGS

FIG. 2 is an exploded view of the container stand as in FIG. 1;

FIG. 3a is a perspective view of a container stand having an interchanged support member;

FIG. 3b is a perspective view of a support member as in FIG. 3a removed from the pole and roller assembly;

FIG. 3c is a sectional view taken along line 3c-3c of FIG. 3a;

FIG. 3d is an isolated view on an enlarged scale taken from FIG. 3c; and

DESCRIPTION OF THE PREFERRED EMBODIMENT

Figure 1:
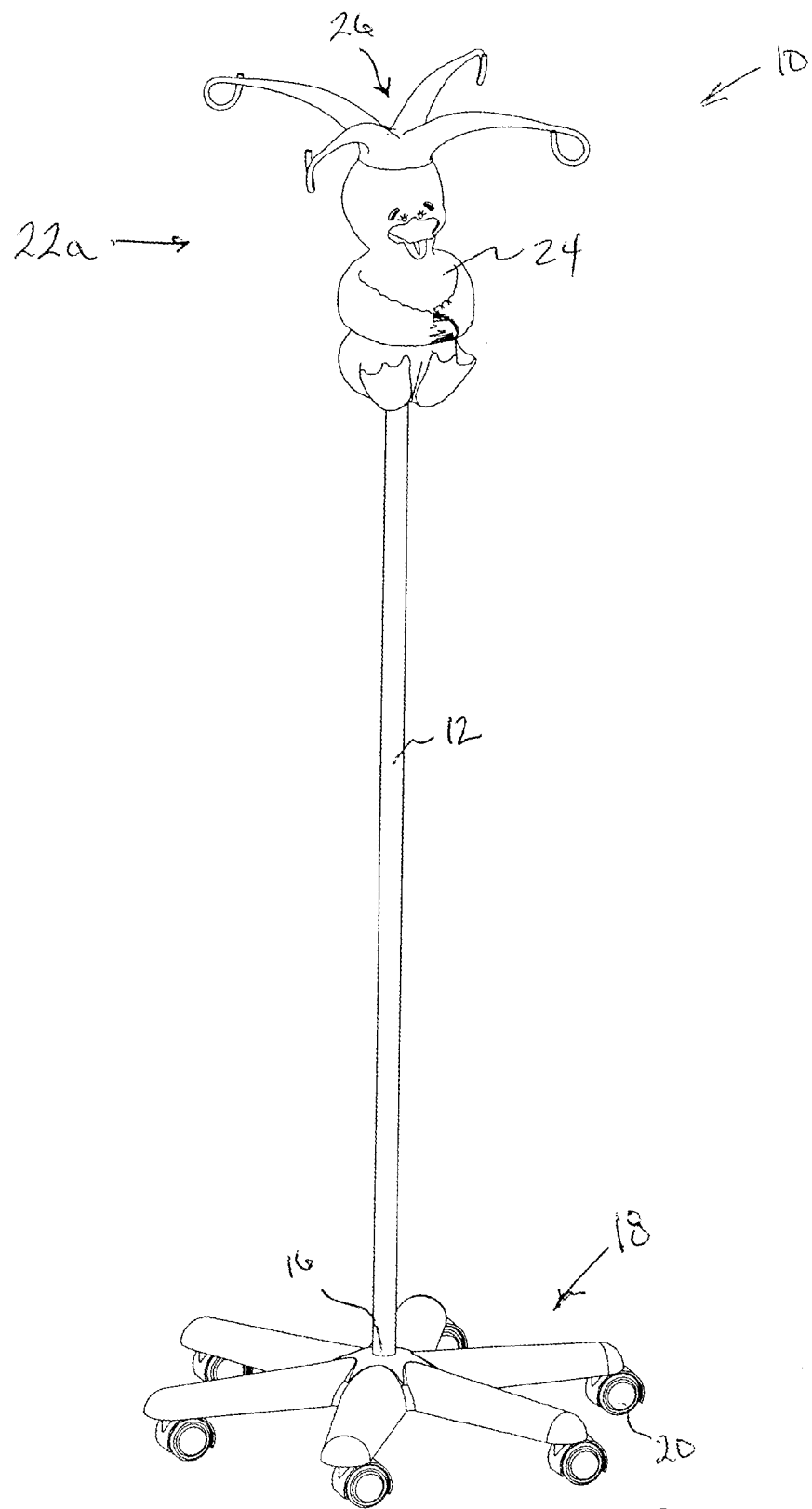
FIG. 1 is a perspective view of an intravenous fluid container stand according to a preferred embodiment of the present invention.

An intravenous fluid container stand according to a preferred embodiment of the present invention will now be described with reference to FIGS. 1 to 4 of the accompanying drawings. The present invention may also be referred to herein as an IV container stand. More particularly, an IV container stand 10 includes an elongate pole 12 having upper 14 and lower 16 ends. (The upper and lower ends may also be referred to herein as the pole upper end and pole lower end, respectively). It is understood that the pole 12 may include a telescopic construction so that it is selectively height adjustable (not shown). For example, the pole 12 may include an upper pole member telescopically receivable into a lower pole member and that may be held in a selected configuration with a pin that may be inserted into a selected adjustment hole (not shown).

A roller assembly 18 may be coupled to the lower end 16 of the pole 12 such that the entire IV container stand 10 may be easily transported to a desired location by pushing or pulling it. Preferably, the roller assembly 18 includes a plurality of castor wheels 20 although other types of wheels may also be suitable.

Figure 3:
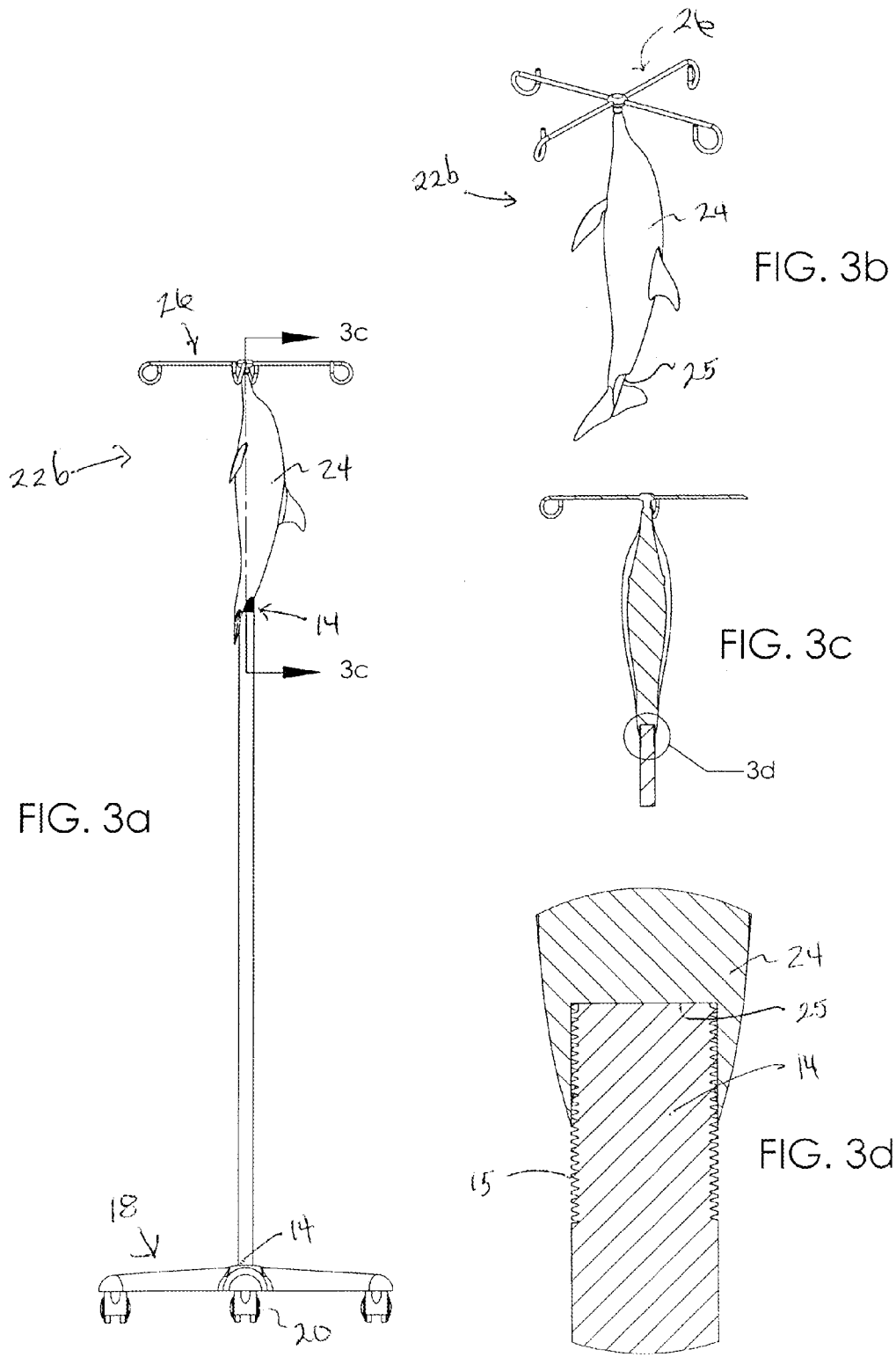

The IV container stand 10 further includes a support member 22a removably coupled to the pole upper end 14 (FIGS. 1 and 2). Forms of the support member other than as shown in FIGS. 1 and 2 are also possible as will described in more detail later. The support member 22a includes a body portion 24 and a hook portion 26 having at least one hook. As shown in FIGS. 1 and 2, the hook portion 26 may be situated atop the body portion 24 although other arrangements are contemplated as well. The hook portion 26 may be integrated with the body portion 24 or be otherwise coupled thereto. As shown in FIGS. 1-3, the hook portion 26 preferably includes more than one hook such that multiple IV fluid containers may be suspended therefrom. Alternately, a support member 22c having an even larger number of hooks may be included (FIG. 4) and interchanged with another support member, as will be described in more detail later.

A means for removably coupling the support member 22a to the pole 12 includes complementary structures of the support member and pole 12. More particularly, the pole upper end 14 presents a male configuration (FIG. 2). In addition, a lower surface of the body portion 24 of the support member 22a defines an opening having a configuration complementary to the configuration of the pole upper end 14 so as to selectively receive the pole upper end 14 therein. The pole upper end 14 and the body portion opening may be dimensioned to fit together in a relatively tight friction fit arrangement.

However, the pole upper end 14 and body portion 24 may be selectively joined in a threaded arrangement. More particularly, the pole upper end 14 may include threads 15 (FIGS. 2 through 3d). Likewise, a lower surface 25 of the body portion 24 of a support member 22b defines an opening having a complementary threaded configuration (FIG. 3d). In use, a support member 22b may be screwed on or off relative to the pole upper end 14.

The body portion 24 of the support member 22a may include a configuration indicative of items selected from the group consisting of an animal, a cartoon character, a mystical character, a superhero, an antique, or the like. As an example, the body portion 24 of the support member 22a shown in FIGS. 1 and 2 is indicative of a "jester duck". Such a configuration is intended to instill feelings of comfort or entertainment to a child who is a patient in a hospital. Similarly, the support member 22b illustrated in FIGS. 3a to 3d is indicative of a dolphin in that sea life may be viewed as a tranquil setting. It should be appreciated that body portions having other animal configurations or cartoon characters are possible. Similarly, antique items (not shown), e.g. an antique vase or the like, may provide feelings of peace and comfort to more elderly patients.

Another aspect of the IV container stand 10 is a unique configuration of each hook itself such that an intravenous fluid container is held securely so as to avoid the possibility of the container slipping or falling. More particularly, the support member 22c (as shown particularly in FIG. 4) includes a body portion 24 and a hook first portion 28 having a first end 30 connected to the body portion 24 and extending outwardly therefrom. A hook second portion 32 is connected to the hook first portion 28 at an end opposed to the first end 30, the hook second portion 32 having a generally arcuate configuration. A hook third portion 34 is connected to the hook second portion 32 and presents a free end 36 that is configured to receive an intravenous fluid container. The hook third portion 34 is situated generally perpendicular to the hook first portion 28.

In use, a user may push or pull the intravenous container stand 10 to a desired location utilizing the roller assembly 18. A desired support member, such as the support members identified as 22a, 22b, or 22c, may be positioned atop the pole 12 as described previously. More particularly, a support member may be threadably or frictionally removed from the pole upper end 14 and another one may be mounted in like manner. For example, the support member 22c having many hooks may be mounted atop the pole 12 when a relatively large number of intravenous fluid container are needed simultaneously. Or, a support member 22a or 22b having a body portion 24 indicative of an animal or fictional character that is comforting for a juvenile patient may be selectively mounted.

It is understood that while certain forms of this invention have been illustrated and described, it is not limited thereto except insofar as such limitations are included in the following claims and allowable functional equivalents thereof.

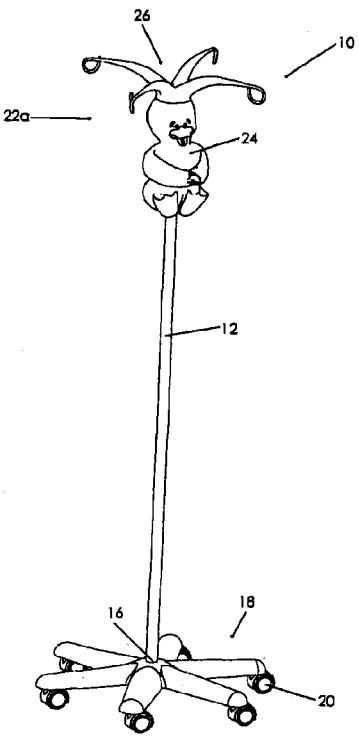

What is claimed is:

1. An intravenous container stand, comprising:
    an elongate pole having opposed upper and lower ends, said upper end of said pole having a threaded configuration;
    a support member including:
        a lower surface defining an opening having a configuration complementary to said threaded configuration of said pole upper end for selectively and removably receiving said pole upper end in a threaded configuration;
        a body portion extending upwardly from said lower surface of said support member and having a configuration indicative of a cartoon character for providing comfort and entertainment to a patient, said body portion extending completely between said lower surface and a body portion upper end;
        a plurality of hooks extending outwardly from said upper end of said body portion and supported by said body portion from which containers of intravenous fluid are selectively suspended without interference with said body portion;
    wherein said lower surface, body portion, and said plurality of hooks include a singular construction that supports said plurality of hooks and respective intravenous fluid containers suspended therefrom;
    wherein each of said plurality of hooks includes:
        a hook first portion having a first end connected to said body portion and extending outwardly;
        a hook second portion having a generally arcuate configuration connected to said hook first portion at an end opposed to said first end, said hook second portion extending generally downwardly from said hook first portion and curving toward said body portion; and
        a hook third portion connected to said hook second portion and having a free end extending upwardly from said said hook second portion, said free end configured to receive an intravenous fluid container, said hook third portion situated generally perpendicular to said hook first portion.

2. The intravenous stand as in claim 1 wherein said body portion includes the configuration indicative of a jester duck.

3. The intravenous stand as in claim 1 wherein said body portion includes the configuration indicative of a super hero character.

4. The intravenous stand as in claim 1 wherein said body portion includes the configuration indicative of an animal for providing comfort and entertainment to the patient.

5. The intravenous stand as in claim 1 further comprising a roller assembly coupled to said lower end of said pole, said roller assembly having a plurality of casters.

* * * * *

UNITED STATES PATENT AND TRADEMARK OFFICE
CERTIFICATE OF CORRECTION

PATENT NO. : 7,556,226 B2 Page 1 of 4
APPLICATION NO. : 11/469993
DATED : July 7, 2009
INVENTOR(S) : Muncie It is certified that error appears in the above-identified patent and that said Letters Patent is hereby corrected as shown below:

The title page, showing an illustrative figure, should be deleted and substitute therefor the attached title page.

On drawing Sheet 1 of 4, replace the informal drawing of Fig 1 with the formal drawing of Fig 1.

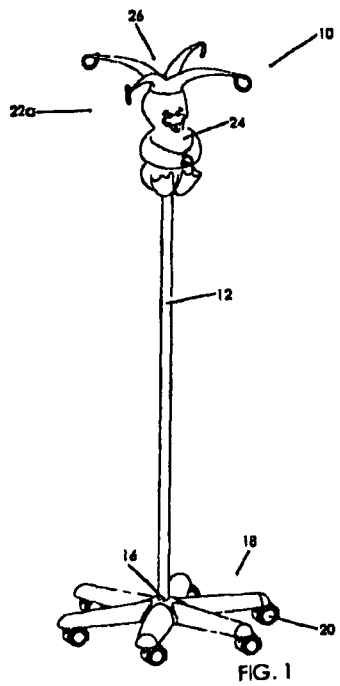

FIG. 1

Signed and Sealed this

Thirty-first Day of August, 2010

David J. Kappos
*Director of the United States Patent and Trademark Office*

CERTIFICATE OF CORRECTION (continued)
U.S. Pat. No. 7,556,226 B2

On drawing Sheet 2 of 4, replace the informal drawing of Fig 2 with the formal drawing of Fig 2.

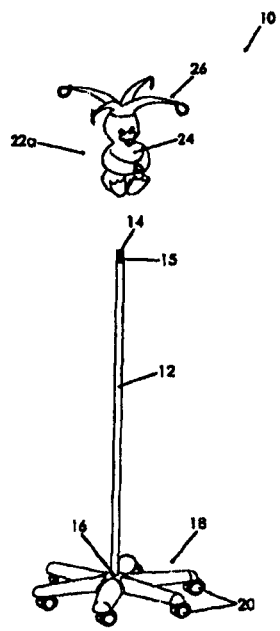

FIG. 2

On drawing Sheet 3 of 4, replace the informal drawing of Fig. 3a, Fig. 3b, Fig. 3c, and Fig. 3d with the formal drawing of Fig. 3a, Fig. 3b, Fig. 3c, and Fig. 3d.

CERTIFICATE OF CORRECTION (continued)
U.S. Pat. No. 7,556,226 B2

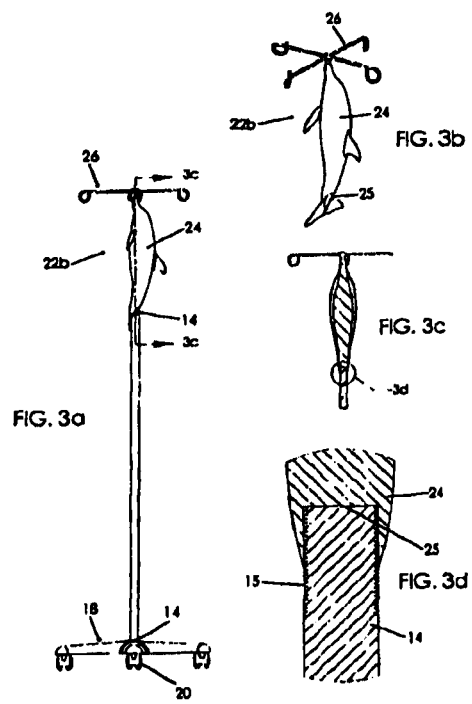

Figure 4:
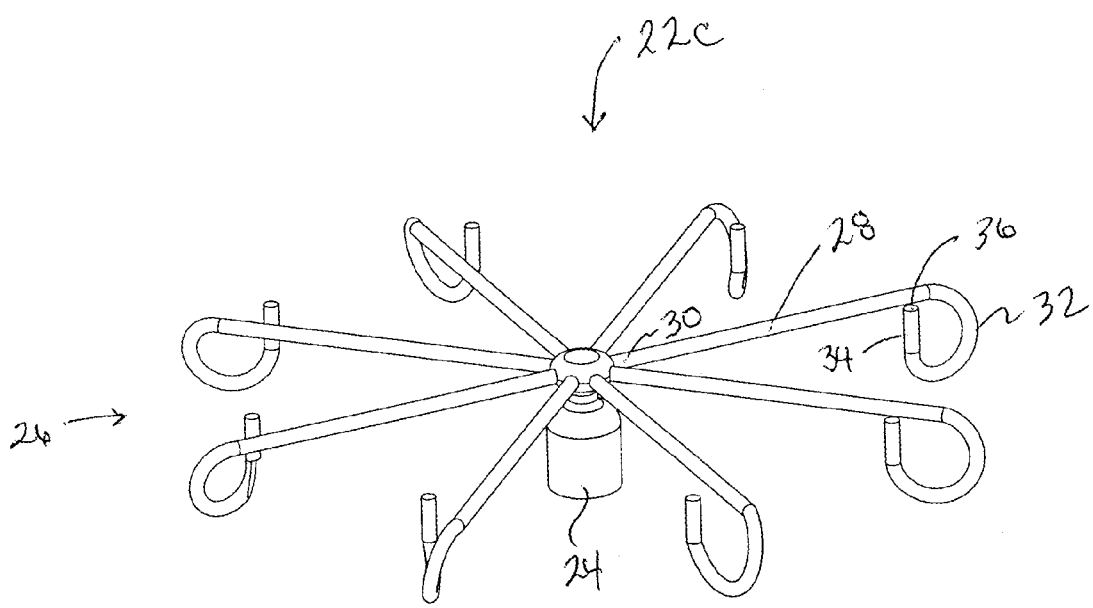
FIG. 4 is a perspective view of another interchangeable support member according to the present invention.

On drawing Sheet 4 of 4, replace the informal drawing of Fig. 4 with the formal drawing of Fig. 4.

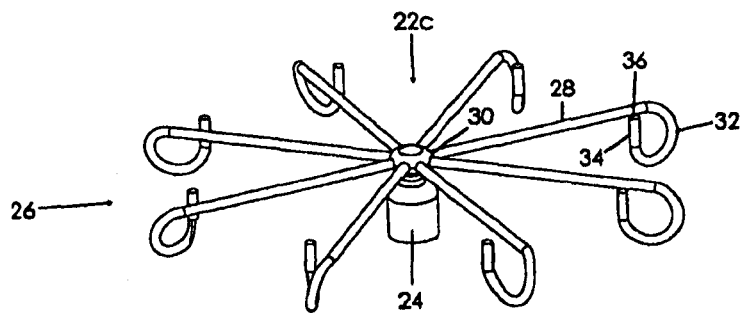

FIG. 4

United States Patent
Muncie

(10) Patent No.: US 7,556,226 B2
(45) Date of Patent: Jul. 7, 2009

(54) INTRAVENOUS FLUID CONTAINER STAND

(76) Inventor: Cindy Muncie, 5922 Centerwood Dr., Crestwood, KY (US) 40014

(*) Notice: Subject to any disclaimer, the term of this patent is extended or adjusted under 35 U.S.C. 154(b) by 0 days.

(21) Appl. No.: 11/469,993

(22) Filed: Sep. 5, 2006

(65) Prior Publication Data

US 2008/0054132 A1 Mar. 6, 2008

(51) Int. Cl.
F16M 11/00 (2006.01)

(52) U.S. Cl. .............................. 248/176.1

(58) Field of Classification Search ............... 248/121, 248/127, 129, 176.1; 211/113, 117, 118, 211/85.5, 85.13, 205, 196
See application file for complete search history.

(56) References Cited

U.S. PATENT DOCUMENTS

| | | | | |
|---|---|---|---|---|
| 1,261,755 A | * | 4/1918 | Forsyth | 248/125.8 |
| 1,606,354 A | * | 11/1926 | Fillion | 362/358 |
| 2,247,774 A | * | 7/1941 | Forsyth | 211/196 |
| 3,460,789 A | * | 8/1969 | Engelsher et al. | 248/146 |
| 3,547,275 A | * | 12/1970 | Engel | 211/205 |
| D290,196 S | * | 6/1987 | Miller | D6/415 |
| 4,725,027 A | | 2/1988 | Bekanich | |
| 4,832,294 A | * | 5/1989 | Eidem | 248/125.8 |
| 5,022,538 A | * | 6/1991 | Richmond et al. | 211/113 |
| D326,374 S | * | 5/1992 | Townsend | D6/412 |
| 5,135,191 A | | 8/1992 | Schmuhl | |
| D329,549 S | * | 9/1992 | Begley et al. | D6/412 |
| 5,421,548 A | * | 6/1995 | Bennett et al. | 248/129 |
| 5,480,036 A | *, | 1/1996 | Opar | 211/45 |
| 5,487,476 A | * | 1/1996 | Barfield | 211/85.23 |
| D369,032 S | * | 4/1996 | Huang et al. | D6/412 |
| D372,156 S | * | 7/1996 | Botsford | D6/548 |
| 5,556,065 A | * | 9/1996 | Wadley | 248/129 |
| 6,375,133 B1 | | 4/2002 | Morrow | |
| 6,386,142 B1 | * | 5/2002 | Holscher et al. | 119/57.8 |
| 6,390,311 B1 | * | 5/2002 | Belokin | 211/204 |
| 2002/0096608 A1 | * | 7/2002 | Cedarberg, III | 248/125.3 |
| 2005/0120525 A1 | * | 6/2005 | Heil et al. | 27/1 |
| 2006/0070968 A1 | * | 4/2006 | Terhune et al. | 211/205 |

* cited by examiner

*Primary Examiner*—Kimberly T Wood
(74) *Attorney, Agent, or Firm*—Dale J. Ream

(57) ABSTRACT

An intravenous container stand according to the present invention includes an elongate pole having opposed upper and lower ends. The container stand includes a support member that may be selectively and removably coupled to the upper end of the pole. The support member includes a body portion coupled to the pole and at least one hook extending outwardly from the body portion for suspending an intravenous fluid container for delivery to the patient. A roller assembly, such a plurality of casters, may be coupled to the lower end of the pole for transporting the container stand to a desired location. The support member is selectively removable and replaceable, such as when different quantities of intravenous containers are needed or for the comfort and entertainment of a patient.

5 Claims, 4 Drawing Sheets